(12) United States Patent
Pytel et al.

(10) Patent No.: US 8,617,526 B2
(45) Date of Patent: Dec. 31, 2013

(54) COSMETIC COMPOSITION, A PHARMACEUTICAL COMPOSITION AND A PROCESS FOR PREPARING SAID COMPOSITIONS

(75) Inventors: Rodrigo Fuscelli Pytel, Cajamar (BR); Luciana Villa Nova Silva, São Paulo (BR); Thiago Braz, Vila Formosa (BR); Flavia da Silva Sena, Cajamar (BR)

(73) Assignee: Natura Cosmeticos S.A., Sao Paulo-SP (BR)

( * ) Notice: Subject to any disclaimer, the term of this patent is extended or adjusted under 35 U.S.C. 154(b) by 993 days.

(21) Appl. No.: 11/910,492

(22) PCT Filed: Apr. 6, 2006

(86) PCT No.: PCT/BR2006/000066
§ 371 (c)(1),
(2), (4) Date: Apr. 7, 2008

(87) PCT Pub. No.: WO2006/105630
PCT Pub. Date: Oct. 12, 2006

(65) Prior Publication Data
US 2009/0016986 A1    Jan. 15, 2009

(30) Foreign Application Priority Data
Apr. 6, 2005    (BR) .................................... 0501241

(51) Int. Cl.
| | |
|---|---|
| *A61K 8/07* | (2006.01) |
| *A61K 8/894* | (2006.01) |
| *A61K 47/48* | (2006.01) |
| *A61K 9/107* | (2006.01) |
| *A61Q 17/04* | (2006.01) |
| *A61Q 19/00* | (2006.01) |

(52) U.S. Cl.
USPC ....................................... 424/70.1; 424/78.17

(58) Field of Classification Search
None
See application file for complete search history.

(56) References Cited

U.S. PATENT DOCUMENTS

| 5,665,368 A | 9/1997 | Lentini et al. | |
| 7,083,800 B1 * | 8/2006 | Terren et al. | 424/401 |
| 2002/0192244 A1 | 12/2002 | Leo et al. | |
| 2004/0223989 A1 * | 11/2004 | Auguste et al. | 424/401 |

FOREIGN PATENT DOCUMENTS

| EP | 0 530 531 | | 3/1993 |
| EP | 0 834 306 | | 4/1998 |
| EP | 1 358 870 | | 11/2003 |
| EP | 1 374 835 | | 1/2004 |
| FR | 2 789 313 | | 8/2000 |
| GB | 2242358 | * | 2/1991 |
| WO | WO 96/28136 | | 9/1996 |
| WO | WO 97/01325 | | 1/1997 |
| WO | WO 99/04711 | * | 9/1999 |
| WO | WO 01/05367 | | 1/2001 |
| WO | WO 2006/012723 | | 2/2006 |
| WO | WO 2006/013414 | | 2/2006 |

OTHER PUBLICATIONS

Flick, E.W. (1995). Cosmetic and Toiletry Formulations, vol. 3 (2nd Edition).. William Andrew Publishing/Noyes. Online version available at: http://knovel.com/web/portal/browse/display?_EXT_KNOVEL_DISPLAY_bookid=591&VerticalID=0.*
International Search Report for PCT Application No. PCT/BR2006/000066; Filed Apr. 6, 2006; Date of Completion Aug. 4, 2006; Date of Mailing Aug. 18, 2006.
Written Opinion for PCT Application No. PCT/BR2006/000066; Filed Apr. 6, 2006; Date of Completion Aug. 4, 2006; Date of Mailing Aug. 18, 2006.
Response to Written Opinion Dated Feb. 6, 2007.
International Preliminary Report on Patentability for PCT/BR2006/000066; Filed Apr. 6, 2006.

* cited by examiner

*Primary Examiner* — Kenneth R. Horlick
*Assistant Examiner* — David Thomas
(74) *Attorney, Agent, or Firm* — Alston & Bird LLP

(57) ABSTRACT

The present invention relates to a cosmetic composition and to a pharmaceutical composition that comprise several agents of topical use and optionally sunscreens. This composition comprises an aqueous medium containing at least one highly polar substance without, however, having the inconveniences noticed in similar compositions of the prior art. These compositions combine the benefits from water-soluble active with the properties of softness and texture that are typical of products that comprise oily-alcoholic, oily or oily-waxy base. Further, the present invention relates to a process for preparing said cosmetic composition and pharmaceutical composition.

32 Claims, No Drawings

COSMETIC COMPOSITION, A PHARMACEUTICAL COMPOSITION AND A PROCESS FOR PREPARING SAID COMPOSITIONS

FIELD OF THE INVENTION

The present invention relates to a cosmetic composition and to a pharmaceutical composition that comprise several agents of topical use and optionally sunscreens. This composition comprises an aqueous medium containing at least one highly polar substance, without, however, having the inconveniences noticed in similar compositions of the prior art.

Further, the present invention discloses a process for preparing the cosmetic and pharmaceutical compositions cited above.

DESCRIPTION OF THE PRIOR ART

The incorporation of aqueous media containing highly polar or ionized substances into galenic forms of oily-alcoholic base as sunscreens in gel, or oily-waxy as lipsticks and lip protectors, technically has a number of difficulties, namely:

low degree or absence of miscibility between the phases: in oily-alcoholic bases, the combination water, oil and alcohol forms a two-phase mixture when the water contents in the ethanol 96° GL is exceeded. This occurs in spite of ethanol and water being miscible and spite of ethanol having good miscibility with several categories of hydrophobic substances;

the absence of miscibility between the phases is also strongly observed in oily-waxy bases, which, in general, do not stand significant water contents. This is empirically observed even when waxes having good moisture-retaining capacity are added to these systems;

adding a substance having high polarity or ionizable to the above-cited bases promotes a significant increase of the polarity of the aqueous phase, making it totally incompatible with the cited galenic formulas;

crystallization: after adding an aqueous medium containing highly polar or ionized substances to the oily-alcoholic or oily-waxy bases, it can be observed both the crystallization of these substances as of some fat-soluble solid substance; this crystallization being caused by varying the available water content or by altering the balance of filler of the whole system; and exudation: this serious problem of migration of oil or water out of oily-waxy bases is, in general, accompanied by crystallization of highly polar or ionized substances.

The applicant indicates hereinafter the relevant documents of the prior art relating to the matter of the present invention.

Document PI 9804595-4 of the same applicant discloses a cosmetic emulsion of the water-in-silicon type, which contains particulate solid cosmetic components and comprises, as an emulsifying system, the association of a primary emulsifier selected from the group consisting of the copoliols such as dimethicone copoliol and a secondary emulsifier selected from lipophilic stearic acids, as for example a polyglyceryl isostearate 4. Further, it is foreseen the possibility of adding other components. It refers to a carrier different from that used in the present invention, since it is restricted to the emulsion, and the present invention comprises other types of bases.

Document U.S. Pat. No. 6,831,191 discloses sun protection formulations for the skin containing some components that act as sunscreens. It is foreseen the addition of some components such as dimethicone copoliol, water, mineral oil, glycols, electrolytes, glyceryl stearate. However, the combinations between these components in the conditions proposed in this document may cause opacity of the alcoholic products and further exudation of the products with oily-waxy base.

Document WO 03/070202 discloses a sun-protection preparation comprising an oil-in-water emulsion, an aqueous or lipophilic phase, an emulsifying agent and UV filters. Like document PI 9804595-4, it refers to a carrier different from that used in the present invention, since it is restricted to the emulsion and the present invention comprises other types of base.

Document CA 2270670 discloses a barrier lotion for the skin, which comprises a long-chain fatty acid, a fatty alcohol, hydrocarbon oil, among other optional components. This lotion is indicated for protecting the skin against agents that irritate it.

Document EP 0 612 517 describes an emulsion that comprises an oily phase with silicone, an aqueous phase and an emulsifying agent that may be a dimethicone copoliol. The aqueous phase comprises a gelling agent, being a mixture of glyceryl and glycol fatty acid esters.

Document U.S. Pat. No. 6,280,712 describes sun-protection formulations for the skin, which contains some components that act as sunscreens. It is foreseen the addition of cetyl dimethicone copoliol, water, among other components.

Document DE 10238450 discloses cosmetic and/or dermatological preparations comprising lipidic particles with lightening agents of the skin. These preparations may also comprise other components such as glycols, glyceryl stearate, esters, alcohols, among others.

As can be seen from the description of the present invention hereinafter, no teaching of the prior art proposes advantages referring to the association of the benefits provided by actives, which are highly polar or ionized, and the galenic forms different from emulsions, resulting in the provision of properties that are achieved exclusively with the use of determined actives through a new carrier, of interest of the users.

SUMMARY OF THE INVENTION

The present invention has the objective of providing a cosmetic composition and a pharmaceutical composition that comprise a base selected from an oily-alcoholic medium, an oily medium and an oily-waxy medium, and further comprise:

triglyceryl 4 isostearate or an isomer thereof;
  dimethicone copoliol or a derivative thereof;
  a lipophilic substance having low or middle polarity;
  a highly polar substance.

Another objective of the present invention is a process for preparing the cosmetic composition and the pharmaceutical composition described above, which comprises the following steps:

a. in a first container, incorporating a lipophilic substance having low or middle polarity, the triglyceryl 4 isostearate or an isomer thereof and dimethicone copoliol or a derivative thereof, under stirring of 500 to 2000 rpm;
  b. keeping the stirring from 5 to 30 minutes until total limpidity of this phase;
  c. adding a highly polar substance, totally solubilized;
  d. keeping the stirring for about 15 minutes.

DETAILED DESCRIPTION OF THE INVENTION

The present invention describes a cosmetic composition and a pharmaceutical composition that comprise highly polar or ionized components and are presented preferably in oily-alcoholic, oily or oily-waxy galenic forms. These galenic forms may be:

oily-alcoholic base: perfumes, fluid sunscreens or gels, among others;
oily base: body oils, bronzer, liquid or gel sunscreens, lip gloss, eyelash masks, among others;
oily-waxy base: lipsticks, lip protector, among others.

In this regard, the main examples of products that can be prepared from the cosmetic or pharmaceutical composition of the present invention are:

body moisturizers;
face moisturizers for diurnal use;
face moisturizers for night use;
anti-body-spot preparations;
anti-body-spot preparations for diurnal use;
anti-face-spot preparations for night use;
body and face cosmetic preparations for children;
after-shave face cosmetic preparation;
cosmetic preparations of localized action, as for example for treating spots or shadows under or around the eyes;
body or face sunscreens; and
pharmaceutical preparations of topical application.

In short, the present invention relates to novel applications and unexpected effects of the combination in media that were not known from the prior art so far. In addition, the present invention relates to the manufacture process that provides said combination of substances. Thus, the compositions of the present invention exhibit excellent technology, so as to provide all the benefits achieved through the combination of media and components that will be described hereinafter, solving the problems of miscibility, crystallization and exudation, which are noticed in compositions that comprise oily-alcoholic, oily and oily-waxy media known so far.

All the description of the composition of the present invention will refer to the cosmetic composition. However, this description should also be understood for the pharmaceutical composition.

Further, the present invention describes a process for preparing the cosmetic composition mentioned above, which enables the incorporation of highly polar or ionized substances in media where they are not miscible. It is known that the incorporation of highly polar or ionized substances in aqueous medium into oily-alcoholic or oily media, in general, causes crystallization of the phases or even crystallization of substances of the medium. Further, it is known that the incorporation of highly polar or ionized substances in an aqueous medium to oily-waxy media generally leads to exudation, drop in hardness of the composition and even to separation of phases. Moreover, the incorporation of highly polar or ionized substances in an aqueous medium to oily-alcoholic, oily or oily-waxy media in incorrect way may result in any of the inconveniences already cited.

Due to the combination of chemical components that will be detailed later, as well as to the process for preparing the cosmetic and pharmaceutical compositions, they do not have the inconveniences noticed in compositions already known from the market used for similar purposes.

The cosmetic and pharmaceutical compositions of the present invention have a range of advantages and characteristics desired in a cosmetic or pharmaceutical product for the skin, some of which are related hereinafter.

1—they have stability; they enable the obtention of stable formulations;

2—they enable the incorporation of actives or sensorial-modifying substance into the galenic forms of the present invention;

3—they do not present crystallization of any ingredient present in the highly polar medium or in the base cosmetic composition, which may be an oily, oily-waxy or oily-alcoholic base;

4—they do not present separation of phases in the oily and oily-alcoholic bases;

5—they do not present exudation in oily-waxy media;

6—they provide an increase in the stability of actives that are optionally present in the highly polar medium due of the protective effect against the action of oxygen (physical barrier formed) which the oily, oily-waxy or oily-alcoholic bases guarantee to this active;

7—they enable the obtention of formulations that can associate the benefits brought by hydrophilic and lipophilic media with galenic form and provide marked sensorial properties (softness, smoothness and texture) of the emulsions (lotion, cream gel, cream, etc.), carriers that conventionally incorporate these benefits;

8—they do not have a photo-irritation and photosensitization potential;

9—they have high resistance to water;

10—the have absence of crystallization, which ensures that the safety and efficacy of the products obtained will be maintained;

11—they present an increase in the stability of water-soluble actives due the protective effect against the action of oxygen (physical barrier formed) guaranteed by the oily-alcoholic or oily-waxy bases; and 12—they enable the obtention of formulations that can associate the benefits already described and the anti-oxidant complex described in the Brazilian patent application PI 0404331-6 belonging to the same applicant. Said anti-oxidant complex comprises a combination of water-soluble and fat-soluble anti-oxidant agents. And thus they provide adequate actuation on both biological media, both hydrophilic and lipophilic, unlike the products presently known on the market. This association provides protection of the skin against the action of solar radiation and acts in an intense way to combat the photo-aging caused by solar radiation.

Cosmetic Composition of the Present Invention

As already said before, the cosmetic composition of the present invention comprises:

triglyceryl 4 isostearate or an isomer thereof;
dimethicone copoliol or a derivative thereof, as dimethicone copolyol alkyl;
a lipophilic substance having low or middle polarity;
optionally an electrolyte.

The galenic forms of oily or oily-waxy bases comprise an electrolyte solubilized in water.

Concisely, the compositions of the present invention comprise at least one cetyl dimethicone copoliol and triglyceryl 4 isostearate dispersed in at least one fat-soluble substance, and water-soluble actives solubilized in water.

In addition to these components, the cosmetic composition of the present invention may further comprise optional components.

The components used in the cosmetic composition of the present invention, as well as other compounds optionally added for the purpose of determining a property yet unachieved, will be described in greater detail hereinafter.

Triglyceryl 4 Isostearate

This component combined with dimethicone copoliol enables the incorporation of the highly polar, already ionized media, to a substance having low or middle polarity.

An example of this preferred type of substance to be added to the cosmetic composition of the present invention is ISOLAN GI 34, produced by Goldschmidt (Degussa Business Unit Care Specialties), which is a polyglyceryl-4 isostearate. This component exhibits an emulsifying property and confers high stability to the composition to which it has been added.

This preferred component is an ester of isostearic acid and polyglycerin-4. Polyglycerin-4 is a glycerin polymer that contains 4 glycerin units bonded by ether bonds. There is a small distribution in the polymerization on degrees. Due to the nature of the partial esterification reaction, any of the hydroxyl groups (approximately 5) of polyglycerol can be esterified with isostearic acid. In the present case, 3 of the hydroxyl groups of polyglycerol are sterified with isostearic acid.

In the preferred embodiments of the present invention, triglyceryl 4 isostearate is added, more preferably ISOLAN GI 34, in an amount ranging from 0.001% to 10.000%, preferably from 0.01% to 4.00%, more preferably from 0.05% to 0.50% by weight, based on the total weight of the cosmetic composition of the present invention.

Dimethicone Copoliol

This component combined with triglyceryl 4 isostearate enables the incorporation of the highly polar media, already ionized, to the low or middle polarity substance.

Examples of this preferred type of substance to be added to the cosmetic composition of the present invention are: dimethicone copoliol alkyls like cetyl dimethicone copoliol.

In the preferred embodiments of the present invention, at least one dimethicone copoliol alkyl is added, more preferably cetyl dimethicone copoliol, in an amount ranging from 0.001% to 10.000%, preferably from 0.01% to 4.00%, more preferably from 0.05% to 0.50% by weight, based on the total weight of the cosmetic composition of the present invention.

Lipophilic Substance Having Low or Middle Polarity

The lipophilic substance having low or middle polarity performs the function of allowing highly polar or ionic substances or media to be incorporated into the compositions of the present invention, and further act as an emollient or sunscreen.

Examples of this preferred type of substance to be added to the cosmetic composition of the present invention are: cosmetic or pharmaceutical components that have a lipophilic nature, preferably that, at temperatures lower than 75° C., are in liquid form. Preferably, it is opted for oils of mineral, synthetic or vegetable origin, esters, sunscreens, branched-chain fatty alcohols and/or acids.

In the preferred embodiments of the present invention, at least one chemical filter is added, liquid at room temperature, or an ester, more preferably 2-ethyl-hexyl p-methoxycinamate and dicapryl carbonate, in an amount ranging from 0.01% to 99.80%, preferably from 0.1% to 70.0%, more preferably from 1.0% to 50.0% by weight, based on the total weight of the cosmetic composition of the present invention.

Highly Polar Substance

The highly polar substance enables the solubilization of the high-polarity ingredients or media present in the cosmetic composition of the present invention.

Examples of this preferred type of substance to be added to the cosmetic composition of the present invention are: substances that form intermolecular interactions by means of hydrogen bridges. Preferably, it is opted for water, glycol or a mixture thereof.

In preferred embodiments of the present invention, it is added preferably water in an amount ranging from 0.001% to 80.00%, preferably from 0.01% to 30.00%, more preferably from 0.05% to 8.00% by weight, based on the total weight of the cosmetic composition of the present invention.

Electrolyte

The electrolyte is present in the oily or oily-waxy galenic forms. This component is solubilized by the highly polar substance. Further, the electrolyte guarantees the increase of the electrolytic charge of the medium. This increase contributes to the stabilization of the system comprised in the cosmetic composition of the present invention.

Examples of preferred electrolytes to be added to the cosmetic composition of the present invention are: salts, preferably an alkali metal chloride, an alkaline-earth metal chloride, an alkali-metal sulfate, an alkaline-earth metal sulfate and combinations thereof.

In the preferred embodiments of the present invention, at least one alkali-metal chloride is added, more preferably sodium chloride, in an amount ranging from 0.001% to 5.00%, preferably from 0.005% to 1.000%, more preferably from 0.02% to 0.40% by weight, based on the total weight of the cosmetic composition of the present invention.

Other Optional Components

In order to provide the cosmetic and pharmaceutical compositions of the present invention with some desired characteristic that has not yet been achieved with the cited components, it may be added optional components that are compatible with their properties. Some of these compounds that may be added to the composition are:

bacteriostatics, bactericidal or antimicrobial;

dyes;

plant extracts: chamomile, rosemary, thyme, calendula, carrot extract, common juniper extract, gentian extract, cucumber extract, among others;

chelating agent like ethylenediaminotetracetyc acid (EDTA) and salts thereof;

pH-adjusting agent like trietanolamine or sodium hydroxide;

skin-conditioning agents;

anti-oxidant agents of lipophilic substances like butyl hydroxy-toluene (BHT), butyl hydroxyanisole (BHA); and other cosmetically accepted components that are compatible with the base composition.

Process for Preparing the Composition of the Present Invention

The process for preparing the cosmetic composition and the pharmaceutical composition of the present invention has the following steps:

a. in a first container, incorporating into the lipophilic substance having low or middle polarity triglyceryl 4 isostearate or a derivative thereof and dimethicone copoliol or a derivative thereof, under stirring of 500 to 2000 rpm;

b. keeping the stirring for 5 to 30 minutes, until limpidity of this phase is achieved;

c. in a second container, adding the highly polar substance and stirring it at a speed of 500 to 200 rpm, until complete solubilization;

d. adding the content of the second container to the first container and stirring at 1000 to 2300 rpm;

e. keeping the stirring for 15 minutes.

Notes:

the whole process should be conducted at temperature ranging from 20 to 30° C.;

In case lipophilic substances having low or middle polarity with melting point higher than room temperature are used, they should be incorporated to the system in pre-molten state.

An example of a process for preparing the cosmetic composition and the pharmaceutical composition of the present invention, which comprises oily-alcoholic base, has the following steps:

a) in a first container, incorporating into the lipophilic substance having low or middle polarity triglyceryl 4 isostearate or a derivative thereof and dimethicone copoliol or derivative thereof under naval stirring ranging from 500 to 2000 rpm;

b) keeping the stirring for 5 to 30 minutes until complete limpidity of this phase is achieved;

c) in a second container, adding the highly polar substance and, optionally, high-polarity ingredients or media to be incorporated and stir at a speed of 500 to 2000 rpm, until complete solubilization;

d) adding the content of the second container to the first container under naval stirring of 1000 to 2300 rpm;

e) keeping the stirring for 15 minutes;

f) preparing the cosmetic or pharmaceutical composition that is desired;

g) incorporating the mixture obtained at the end of the preparation of the cosmetic or pharmaceutical composition under naval stirring of 500 to 2000 rpm. In this step, the speed adjustment should be made on the basis of the viscosity of the system.

Notes:
- The whole process should be conducted at temperatures ranging from 20 to 30° C.;
- In case lipophilic substances having low or middle polarity with melting point higher than room temperature are used, they should be incorporated to the system in pre-molten state.

An example of a process for preparing the cosmetic composition and the pharmaceutical composition of the present invention that comprise oily base has the following steps:

a) in a first container, incorporate into the lipophilic substance (s) having low or middle polarity triglyceryl 4 isostearate or a derivative thereof and dimethicone copoliol or a derivative thereof under naval stirring, which should range from 500 to 2000 rpm;

b) keeping the stirring for 5 to 30 minutes until complete limpidity of this phase is achieved;

c) in a second container, adding the highly polar substance and the high-polarity ingredients or media to be incorporated and stirring at a speed of 500 to 2000 rpm until complete solubilization;

d) adding to the second container the electrolyte and stir at a speed of 500 to 2000 rpm for 15 minutes;

e) adding the components of the second container to the first container under naval stirring of 1000 to 2300 rpm;

f) keeping stirring for 15 minutes;

g) preparing the cosmetic or pharmaceutical composition desired;

h) incorporating the mixture obtained at the end of the preparation of the cosmetic or pharmaceutical composition under naval stirring of 500 to 200 rpm. In this step, the speed adjustment should be made on the basis of the viscosity of the system;

Notes:
- The whole process should be conducted at temperatures ranging from 20 to 30° C.;
- In case lipophilic substances having low or middle polarity with melting point higher than room temperature are used, they should be incorporated to the system in pre-molten state.

An example of a process for preparing the cosmetic composition and the pharmaceutical composition of the present invention that comprise oily-waxy base has the following steps:

a) in a first container incorporate to the lipophilic substance (s) having low or middle polarity triglyceryl 4 isostearate or a derivative thereof and dimethicone copoliol or a derivative thereof under naval stirring, which should be of 500 to 2000 rpm;

b) keeping the stirring for 5 to 30 minutes until complete limpidity of this phase is achieved;

c) in a second container, adding the highly polar substance and the high-polarity ingredients or media (Phase 5) to be incorporated and stirring at a speed of 500 to 2000 rpm until complete solubilization;

d) adding to the composition of (c) the electrolyte and stirring at a speed of 500 to 2000 rpm for 15 minutes;

e) adding the components of the second container to the first container under naval stirring of 1000 to 2300 rpm;

f) keeping the stirring for 15 minutes;

g) heating up to a temperature of 75° C., keeping the same stirring;

h) preparing the cosmetic or pharmaceutical composition desired;

i) incorporating the mixture obtained at the end of the preparation of the cosmetic or pharmaceutical composition, under naval stirring of 20 to 300 rpm and anchor of 10 to 60 rpm. In this phase, the mixture obtained and the cosmetic or pharmaceutical composition should be at a temperature of 75° C. and the speed adjustment should be made on the basis of the viscosity of the system. Hot-bottling the product.

Notes:
- the steps a) to h) should be conducted at temperatures ranging from 20 to 30° C.;
- In case lipophilic substances having low or middle polarity with melting point higher than room temperature are used, they should be incorporated to the system in pre-molten state.

EXAMPLES OF THE COSMETIC COMPOSITION OF THE PRESENT INVENTION

The examples given below are preferred embodiments of the cosmetic compositions of the present invention and should not be construed as being limitations thereof. Thus, many other variations of composition may be carried out within the protection scope delimited by the set of claims.

Example 1

Moisturizing Lip Protector SPF 30

This composition was prepared according to the process of the present invention, which comprises the following steps:

a) in a first container, incorporate into the lipophilic substance (s) having low or middle polarity (Phase 1) triglyceryl 4 isostearate and cetyl dimethicone copoliol (Phase 2) under naval stirring, which should range from 500 to 2000 rpm;

b) keeping the stirring for 5 to 30 minutes until complete limpidity of this phase;

c) in a second container, adding the highly polar substance (Phase 4) and the high-polarity ingredients or media (Phase 5) to be incorporated and stirring at a speed of 500 to 2000 rpm until complete solubilization;

d) adding to the second container the electrolyte (Phase 3) and stirring at a speed ranging from 500 to 2000 rpm for 15 minutes;

e) adding the components of the second container to the first container under naval stirring, which should range from 1000 to 2300 rpm;

f) keeping the stirring for 15 minutes;

g) heating up to 75° C., keeping the same stirring and adding to the component of Phase 6 to the mixture;

h) in a third container, adding the components of Phase 7 and melting. Keeping the temperature at 75° C.;

i) incorporating the mixture obtained at the end of the preparation of the cosmetic or pharmaceutical composition, under naval stirring, which should range from 20 to 300 rpm and anchor of 10 to 60 rpm. In this phase, the mixture obtained and the cosmetic or pharmaceutical composition should be at a temperature of 75° C. and the speed adjustment should be made on the basis of the viscosity of the system. Hot-bottling the product.

Notes:
- the steps a) to h) should be conducted at temperatures ranging from 20 to 30° C.;
- In case lipophilic substances having low or middle polarity with melting point higher than room temperature are used, they should be incorporated to the system in pre-molten state.

| Components | Massic composition (% by weight) | Phase |
|---|---|---|
| Dicapryl carbonate | Qsp 100.00 | 1 and 7 |
| Microcrystalline wax | 16.60 | 7 |
| Refined camauba wax | 5.18 | 7 |
| Macamat wax | 3.85 | 7 |
| USP Type I bee wax | 5.50 | 7 |
| Ozokerite wax | 3.72 | 7 |
| Glyceryl behenate | 1.00 | 7 |
| PVP eicosano copolymer | 2.70 | 7 |
| 2-ethyl-hexyl p-methoxycinamate | 10.00 | 7 |
| Bis-ethyl-hexyloxyphenol methoxyphenol triazine | 1.50 | 7 |
| Benzophenone 3 | 6.00 | 7 |
| Octyl triazone | 5.00 | 7 |
| Lycopen extracted from tomato | 0.002 | 1 |
| Vitamin E acetate | 0.20 | 1 |
| BHT | 0.05 | 7 |
| Sodium chloride | 0.04 | 3 |
| Aluminum octenylsuccinate starch | 10.00 | 6 |
| Cetyl dimethicone copoliol | 0.12 | 2 |
| Triglyceryl-4 isostearate | 0.12 | 2 |
| Biosaccharide-2 gum | 0.20 | 5 |
| Biosaccharide 3 gum | 0.20 | 5 |
| Methylparaben | 0.20 | 7 |
| Propylparaben | 0.10 | 7 |
| Coffee extract (Coffea robusta) | 0.002 | 4 |

| Components | Function |
|---|---|
| Dicapryl carbamate | Emollient - lipophilic substance having low or middle polarity |
| Microcrystalline wax | Consistency agent |
| Refined camauba wax | Consistency agent |
| Macamat wax | Consistency agent |
| USP Type I bee wax | Consistency agent |
| Ozokerite wax | Consistency agent |
| Glyceryl behenate | Consistency agent |
| PVP eicosano copolymer | Film forming agent |
| 2-ethyl-hexyl p-methoxycinamate | Sunscreen - lipophilic substance with low or middle polarity |
| Bis-ethyl-hexyloxyphenol methoxyphenol triazine | Sunscreen |
| Benzophenone 3 | Sunscreen |
| Octyl triazone | Sunscreen |
| Lycopen extracted from tomato | Anti-oxidant agent |
| Vitamin E acetate | Anti-oxidant agent |
| BHT | Anti-oxidant agent |
| Sodium chloride | Viscosity adjusting agent - electrolyte |
| Aluminum octenylsuccinate starch | Sensorial-modifying agent |
| Cetyl dimethicone copoliol | Emulsifying agent |
| Triglyceryl-4 isostearate | Emulsifying agent |
| Biosaccharide-2 gum | Active - a high-polarity substance |
| Biosaccharide-3 gum | Active - a high-polarity substance |
| Methylparaben | Preservative |
| Propylparaben | Preservative |
| Coffee extract (Coffea robusta) | Anti-oxidant |

Example 2

Ultra Gel Protector

SPF 30

This composition was prepared in accordance with the process of the present invention, which comprises the following steps:

a) in a first container, incorporating into the lipophilic substance (s) having low or middle polarity (Phase 1), previously molten, triglyceryl-4 isostearate and cetyl dimethicone copoliol (Phase 2) under naval stirring, which should range from 500 to 2000 rpm;

b) keeping the stirring for 5 to 30 minutes until complete limpidity of this phase is achieved;

c) in a second container, adding the highly polar substance (Phase 4) and the high-polarity ingredients or media (Phase 3) to be incorporated;

d) stirring the above-described system at a speed of 500 to 2000 rpm until complete solubilization;

e) adding the components of the second container to the first container under naval stirring ranging from 1000 to 2300 rpm;

f) keeping the stirring for 15 minutes;

g) to the alcohol (Phase 5) adding the other components of the formulation (Phase 6);

h) incorporating the mixture obtained in item e) to at the end of the preparation of the cosmetic or pharmaceutical composition obtained in item g), under naval stirring of 500 to 2000 rpm. In this step the speed adjustment should be made on the basis of the viscosity of the system.

Notes:
- the whole process should be conducted at temperatures ranging from 20 to 30° C.;
- in case lipophilic substances having low or middle polarity with melting point higher than room temperature, they should be incorporated to the system ion pre-molten state.

| Components | Massic composition (% by weight) | Phase |
|---|---|---|
| 96° GL ethyl alcohol | Qsp 100 | 5 |
| Hydroxypropyl cellulose | 1.20 | 6 |
| Lycopen extracted from tomato | 0.002 | 6 |
| Vitamin E acetate | 0.20 | 1 |
| Coffee extract (Coffea robusta) | 0.002 | 4 |
| PVP/VA E-735 copolymer | 0.30 | 6 |
| Biosaccharide -2 gum | 0.20 | 3 |
| Biosaccharide-3 gum | 0.20 | 3 |

-continued

| Components | Massic composition (% by weight) | Phase |
|---|---|---|
| BHA | 0.05 | 1 |
| Benzophenone 3 | 4.00 | 1 |
| Cetyl lactate | 1.00 | 1 |
| Octyl triazone | 3.00 | 1 |
| Butyl methoxydibenzoylmethane | 2.00 | 1 |
| 2-ethyl-hexyl p-methoxycinamate | 9.00 | 1 |
| Cetyl dimethicone copoliol | 0.12 | 2 |
| Triglyceryl-4 isostearate | 0.12 | 2 |

| Components | Function |
|---|---|
| 96° GL ethyl alcohol | Carrier - highly polar substance |
| Hydroxypropyl cellulose | Thickener |
| Lycopen extracted from tomato | Anti-oxidant agent |
| Vitamin E acetate | Anti-oxidant agent |
| Coffee extract (*Coffea robusta*) | Anti-oxidant agent |
| PVP/VA E-735 copolymer | Film forming agent |
| Biosaccharide- 2 gum | Active - high polarity substance |
| Biosaccharide- 3 gum | Active - high polarity substance |
| BHA | Anti-oxidant agent |
| Benzophenone 3 | Sunscreen |
| Cetyl lactate | Emollient |
| Octyl triazone | Sunscreen |
| Butyl methoxydibenzoylmethane | Sunscreen |
| 2-ethyl-hexyl p-methoxycinamate | Sunscreen - a lipophilic substance having low or middle polarity |
| Cetyl dimethicone copoliol | Emulsifier |
| Triglyceryl isostearate 4 | Emulsifier |

Example 3

Gel Sunscreen

| Phase | Component | Massic composition (% by weight) |
|---|---|---|
| 1 | Demineralized water | 1.50 |
| 1 | Coffee extract (*Coffea robusta*) | 0.30 |
| 2 | 2-ethylhexyl p-methoxycinamate | 3.50 |
| 2 | Cetyl dimethicone copoliol | 0.35 |
| 2 | Triglyceryl 4 isostearate | 0.22 |
| 3 | 96° GL ethyl alcohol | Qsp 100% |
| 4 | Hydroxypropylcellulose | 2700-4200 |
| 5 | 2-ethyl-hexyl p-methoxycinamate | 4.00 |
| 5 | BHA | 0.05 |
| 5 | Benzophenone 3 | 4.00 |
| 5 | Octyl triazone | 3.00 |
| 6 | Vitamin E acetate | 2.00 |

| Component | Function |
|---|---|
| Demineralized water | Carrier - a highly polar substance |
| Coffee Extract (*Coffea robusta*) | Anti-oxidant agent |
| 2-ethyl-hexyl p-methoxycinamate | Sunscreen - a lipophilic substance having low or middle polarity |
| Cetyl dimethicone copoliol | Emulsifier |
| Triglyceryl - 4 isostearate | Emulsifier |
| 96° GL ethyl alcohol | Carrier - a highly polar substance |
| Hydroxypropylcellulose | Thickener |
| BHA | Anti-oxidant agent |
| Benzophenone 3 | Sunscreen |
| Octyl triazone | Sunscreen |
| Vitamin E acetate | Anti-oxidant agent |

Example 4

Lip Protector

| Phase | Component | Massic composition (% by weight) |
|---|---|---|
| 1 | Demineralized water | 1.70 |
| 1 | Coffee extract (*Coffea robusta*) | 0.30 |
| 1 | Sodium chloride | 0.05 |
| 2 | Dicapryl carbonate | 4.00 |
| 2 | Cetyl dimethicone copoliol | 0.28 |
| 2 | Triglyceryl-4 isostearate | 0.37 |
| 3 | 2-ethyl-hexyl p-methoxycinamate | 7.00 |
| 3 | Vitamin E acetate | 2.00 |
| 3 | Dicapryl carbonate | Qsp 100% |
| 3 | Microcrystalline wax | 16.60 |
| 3 | Carnauba wax | 6.00 |
| 3 | Bee wax | 8.00 |
| 3 | Ozokerite wax | 5.00 |
| 3 | Glyceryl behanate | 1.00 |
| 3 | Bis-ethyl-hexyloxyphenol methoxyphenyl triazine | 3.00 |
| 3 | Octyl triazine | 3.00 |
| 3 | Methylparaben | 0.20 |
| 3 | Propylparaben | 0.10 |
| 3 | BTH | 0.05 |

| Component | Function |
|---|---|
| Demineralized water | Carrier - high polarity substance |
| Coffee extract (*Coffea robusta*) | Anti-oxidant agent |
| Sodium chloride | Speed adjusting agent - electrolyte |
| Dicapryl carbonate | Emollient - lipophilic substance having low or middle polarity |
| Cetyl dimethicone copoliol | Emulsifier |
| Triglyceryl-4 isostearate | Emulsifier |
| 2-ethyl-hexyl p-methoxycinamate | Sunscreen - a lipophilic substance having low or middle polarity |
| Vitamin E acetate | Anti-oxidant agent |
| Microcrystalline wax | Consistency agent |
| Carnauba wax | Consistency agent |
| Bee wax | Consistency agent |
| Ozokerite wax | Consistency agent |
| Glyceryl behenate | Consistency agent |
| Bis-ethyl-hexyloxyphenol methoxyphenyl triazine | Sunscreen |
| Octyl triazine | Sunscreen |
| Methylparaben | Preservative |
| Propylparaben | Preservative |
| BHT | Anti-oxidant agent |

Tests of the Cosmetic Composition of the Present Invention

I. The Composition Used in the Tests Described Hereinafter is that defined in Example 1—Moisturizing Lip Protector SPF 30

1—a Clinical, Mono-Blind, Randomized Study, Parallel Control of the Determination of the Sun Protection Factor (SPF) Before and after Immersion into Water (High Resistance to Water)

The objective of this test is to determine the sun protection factor (SPF) before and after immersion into water of the above-cited cosmetic composition.

10 female volunteers with age between 19 and 40 years (average of 29 years), phototypes I, II and III, were selected. Volunteers with a history of phototoxic and photoallergic reactions, use of medicaments liable to produce abnormal cutaneous response, presence of sunburn, bronzed, unequal skin tone, spots, nevus, seborrheic keratosis or excess hair at the site of the test, pregnancy or breast-feeding were excluded 3 areas of 35 cm² were demarked in the infra-scapular region of the volunteers. Standard sunscreen and the cosmetic composition were applied in regions adjacent in the amount of 0.07 g homogeneously. Subsequently, the areas were irradiated and dipped into water. The exposure times varied for each area and were annotated. With these data obtained, the SPF was calculated.

Result: the product presented SPF 35.6. Thus, it was passed as SPF 30.0 and has high resistance to water.

2. Dermatological Evaluation of Topical Comedogenic Potential

This study has the function of evaluating the degree of comedogenicity caused by the application of the composition to the skin. "Comedogenicity" is the production of comedones on the ear of rabbits or on the back of subject. Comedones are commonly known as blackheads, being constituted by keratin and sebum, forming amorphous masses that fill up the pilosebaceus follicle. The conditions that determine its appearance are the obstruction of the follicle by hyperkeratosis and the increase in the production of the sebum by the sebaceous glands.

Examples of comedogenic substances are mineral oils, lanolin, squalene, cocoa butter and oleic acid.

For this study, male and female volunteers of phototypes V and VI and with age ranging from 21 to 60 years were selected. The following material was used: semi-occlusive dressings, anti-allergic impermeable sticking plaster, physiological solution, microscope slides, cyanoacrylate glue, an ordinary optical microscope, a magnifying glass (20×), samples of the product under study.

The method used for evaluating the comedogenicity of the cosmetic composition was the occlusive patch test or contact or epicutaneous tests. 0.2 ml of the cosmetic composition was applied to the volunteer's back and the control with physiological solution. The occlusion of this area followed with the non-absorbent cotton fabric and anti-allergic impermeable sticking plaster. This procedure was repeated every 72 hours for 28 days.

The laboratory evaluation was effected after this 28-day period. Follicular biopsies were carried out through application of the cyanoacrylate glue in the places where the cosmetic composition was deposited and to the control place. The slides containing the material obtained in the biopsy were analyzed and compared through microscopic examination. The evaluations of the slides were effected by a trained expert, supervised by a dermatologist.

The clinical evaluations were carried out by a dermatologist in the beginning of the study and immediately after withdrawal of the occlusive patch tests every 48 hours. Said evaluations were made with the aid of a magnifying glass with white fluorescent illumination. All the areas of application of the products and the control area were evaluated.

Result: The tests carried out with respect to the samples of the composition proved absence of comedogenicity therein.

3. Dermatological Evaluation of Topical Photo-Irritating and Photo-Sensitization Potential This study has the function of proving the absence of photo-irritating potential of the cosmetic composition on the skin.

The irritation potential of a product depends upon a several of variables: the components of the composition, the concentration of each of the components, absorption of said components by the skin, the amount applied to the skin, the state in which the skin is at the time of application, the mode and the frequency of application of the product to the skin and the inherent cumulative effect of the product.

I. Research on Photo-Irritation

The patch test is the main tool used in the diagnosis of a reaction caused by a cosmetic, and in the research on allergenicity. In the research of allergenicity, the following clinical tests are involved: primary and accumulated dermal irritability, skin sensitization, phototoxicity and photoallergy. They consist of repeated applications of the product to the skin and have the function of detecting possible irritations or induction of sensitization.

In order to carry out the tests for allergenicity, 25 female and male volunteers of phototypes I, II and III, with ages ranging from 18 to 60 years, were selected, excluding subjects who had diseases of the skin, injuries or nervus on the back, pregnancy and breast-feeding.

For effecting this study, the following material was used: semi-occlusive dressings composed by a hypoallergenic adhesive card for patch test with filter paper disc of 1.0 cm² duly identified, semi-permeable sticking plaster for occlusion, cellophane adhesive tape for superficial scarification, physiological solution and samples of the cosmetic composition.

All the volunteers were subjected to scarification of the horny layer on the volar face of the forearm. Occlusive dressings containing 0.2 ml of the cosmetic composition and of the control were applied to each area of 1 cm² of the paper disc. These discs were fixed to the back of the volunteers with the aid of sticking plaster. After two hours, the dressings were removed and the region was irradiated with UVA.

II. Research on Sensitization

Occlusive dressings containing 0.2 ml of the cosmetic composition and of the control were applied to each area of 1 cm² of the paper disc. After 24 hours, the dressings were removed and after 30 minutes the region was irradiated with UVA.

The applications were carried out every 24 or 48 hours for two consecutive weeks. The patch test was removed by the researchers 24 hours after application thereof. After this series, a 2-week rest period followed, when no patch was applied. Then, a simple patch of the sample was applied to the back of the volunteers in the virgin area. The patch test was removed by the researchers after 24 hours of contact with the skin, which was irradiated, and the reactions were annotated.

Result: the tests carried out evidenced absence of skin sensitization and no irritation process or sensitization process was identified during the study.

4. Dermatological Evaluation of Topical Compatibility

This study has the function of proving the absence of any potential of primary dermal irritation potential, accumulated dermal irritation and dermal sensitization potential of the formulation.

For carrying out the allergenicity tests, 50 male and female volunteers with age ranging from 18 to 60 years were selected, excluding subjects who had any disease of the skin, injuries or nevus on the back, pregnancy or breast-feeding.

In order to effect this study, the following material was used: semi-occlusive dressings composed by filter paper discs of 1.0 cm² duly identified, hypoallergenic semi-permeable sticking plaster for occlusion, physiological solution and samples of the cosmetic composition.

The following clinical researches were carried out.

I. Research on Primary Irritability 0.2 ml of the cosmetic composition was applied to each area of 1 cm² of the filter paper disc, and to the control disc a saline solution was applied. These discs were fixed to the volar face of the forearms of the volunteers with the aid of sticking plaster.

The testing method used was the occlusive patch test. The sites of application of the test were the back of the volunteers, duly protected. The occlusive patch test was removed by the researchers after 48 hours of contact with the skin, and the reactions were annotated 30 minutes after removal thereof.

II. Research on Accumulated Irritability

The sample was applied always in the same region, on the back, duly protected. Every 48 hours, the volunteers returned for removal of the dressings, reading of the sites and re-application of the dressings to the same sites, for 3 consecutive weeks, in a total of 9 applications. The sample was re-applied onto the skin always at the same place, and the reactions were annotated.

III. Research on Sensitization

After 9 consecutive applications, a 2-week rest period followed, when no patch was applied. After this rest interval, semi-occlusive dressings containing the product under study were applied and the control in a virgin area, that is to say, a place where no patch had been applied. The test was removed by the researchers after 48 hours of contact with the skin, and the reactions were annotated 30 minutes after removal thereof.

After 24 hours, the last reading was effected.

Result: no potentials of primary dermal irritation, accumulated dermal irritation or dermal sensitization were observed.

5. Study of Stability—Oily-Waxy Galenic Form

The study of stability of cosmetic products has the objective of supplying data that indicate the degree of relative stability of a product in environmental conditions to which they may be subject from its manufacture until the end of its validity term.

The stability of a product is relative, since it varies according to the time and to some factors that accelerate or reduce the alterations in the parameters that characterize the product. These variations may be considered acceptable, as long as they occur within determined limits (specifications).

Through studies of stability under conditions of accelerated aging of the product, the validity term thereof can be estimated: a product that is kept within the specifications after 1 month at a temperature of 45° C. or 3 months at a temperature of 37° C. can have a validity term stipulated in 2 years.

In the study of stability of a product under conditions of accelerated aging, it is expected that, under determined conditions, some variations in the evaluated parameters will occur; however, these variations should remain within the specified limits.

In the evaluation of stability of the finished product under conditions of accelerated aging, the following parameters were analyzed:

Organoleptic Parameters

Appearance: the samples subjected to the conditions of 37° C., 5° C., 25° C. and sunlight for 3 months, the samples subjected to 45° C. for 1 month and the samples subjected to the cycle conditions of 25° C./−5° C., 25° C./37° C. and −5° C. for 1 month did not present significant variations.

Color: the samples subjected to the conditions of 37° C., 5° C., 25° C. and sunlight for 3 months, the samples subjected to 45° C. for 1 month and the samples subjected to the cycle conditions of 25° C./−5° C., 25° C./37° C. and −5° C./37° C. for 1 month did not present significant variations.

Odor: the samples subjected to the conditions of 37° C., 5° C., 25° C. and sunlight for 3 months, the samples subjected to 45° C. for 1 month and the samples subjected to the cycle conditions of 25° C./−5° C., 25° C./37° C. and −5° C./37° C. for 1 month did not present significant variations.

Result: Estimated Validity Term: 2 years

II. The Composition Used in the Tests Described Hereinafter is that Defined in Example 2 Ultra Gel Protector SPF 30.

1. Clinical, Mono-Blind, Randomized Study, Parallel Control of the Determination of the Sun Protection Factor (SPF) Before and after Immersion into Water (High Resistance to Water)

The objective of this test is to determine the sun protection factor (SPF) before and after immersion of the above-cited cosmetic composition into water.

10 female volunteers with ages ranging from 22 to 46 years (average of 29 years), of phototypes I, II and III, were selected. The volunteers with a history of phototoxic and photoallergic reactions, use of medicament liable to cause abnormal skin reaction, presence of sunburn, bronzed, with uneven skin tone, spots, nevus, seborrheic keratosis or excess hair at the test site, pregnancy and breast-feeding were excluded.

3 areas of 35 $cm^2$ were demarked in the infra-scapular region of the volunteers. Standard sunscreen and the cosmetic composition were applied in adjacent regions in an amount of 0.07 g homogeneously. Subsequently, the areas were irradiated and dipped into water. The exposure times varied for each area and were annotated. With these data obtained, the SPF was calculated.

Result: the product exhibited SPF 34.0. Thus, it passed as SPF 30.0 and has high resistance to water.

2. Dermatological Evaluation of Topical Comedogenic Potential

This study has the function of evaluating the degree of comedogenicity caused by application of the composition to the skin.

For this study, male and female volunteers of phototypes V and VI and with ages ranging from 21 to 60 years were selected. The following material was used: semi-occlusive dressings, anti-allergic impermeable sticking plaster, physiological solution, microscope slides, cyanoacrylate glue, an ordinary optical microscope, a magnifying glass (20×), samples of the product under study.

The method used for evaluating the comedogenicity of the cosmetic composition was the occlusive patch test or contact or epicutaneous tests. 0.2 ml of the cosmetic composition was applied to the back of the volunteers and the control with physiological solution. The occlusion of this area with a non-absorbent cotton fabric and impermeable anti-allergic sticking plaster followed. This procedure was repeated every 72 hours for 28 days.

The laboratory evaluation was effected after this 28-day period. Follicular biopsies were carried out through application of the cyanoacrylate glue, at the places where the cosmetic composition had been deposited and at the place of control. The slides containing the material obtained in the biopsy were analyzed and compared through microscopic examination. The evaluations of the slides were carried out by a trained expert, supervised by a dermatologist.

The clinical evaluations were effected by a dermatologist in the beginning of the study and immediately after removal of the occlusive patch tests every 48 hours. Said evaluations were made with the aid of a magnifying glass with white fluorescent illumination. All the application areas of the products and the control area were evaluated.

Result: the tests carried out with respect to the samples of the composition proved the absence of comedogenicity therein.

3. Dermatological Evaluation of Photoirritation Potential and Topical Photosensitization Potential This study has the function of proving the absence of photoirritation potential of the cosmetic composition on the skin.

I. Research on Photoirritation

The patch test is the main tool used in the diagnosis of reaction caused by cosmetic and in the research on allergenicity. In the research of allergenicity, the following clinical tests are involved: primary and accumulated dermal irritability, skin sensitization, phototoxicity and photoallergy. They consist of repeated applications of the product to the skin and have the function of detecting possible irritations or induction of sensitization. It is indicated to carry out this use test after approval of the product in the patch tests. With the use tests, it can be evaluated, in addition to allergenicity, sensorial characteristics of the products, that is to say, their performance.

For carrying out the tests for allergenicity, 25 male and female volunteers with phototypes I, II and III, with ages ranging from 18 to 60 years, were selected excluding subjects who had any disease of the skin, injuries or nevus on the back and pregnancy or breast-feeding.

In order to effect this study, the following material was used: semi-occlusive dressings composed by a hypoallergenic adhesive card for patch test with filter paper discs of 1.0 $cm^2$ duly identified, hypoallergenic semi-permeable sticking plaster for occlusion, cellophane adhesive tape for surface scarification, physiological solution and samples of the cosmetic composition.

All the volunteers were subjected to scarification of the horny layer on the volar face of the forearm. Occlusive dressings containing 0.2 ml of the cosmetic composition and of the control were applied to each area of 1 $cm^2$ of the paper disc. These discs were fixed to the back of the volunteers with the aid of sticking plaster. After two hours, the dressings were removed, and the region was irradiated with UVA.

II. Research on Sensitization

Occlusive dressings containing 0.2 ml of the cosmetic composition and of the control were applied to each area of 1 $cm^2$ of the paper disc. After 24 hours, the dressings were removed, and after 30 minutes the region was irradiated with UVA.

The applications were carried out every 24 or 48 hours for two consecutive weeks. The patch test was removed by the researchers 24 hours after application thereof. After this series, a two-week rest period followed, when no patch was applied. Then, a simple patch of the sample was applied to the back of the volunteers, in the virgin are. The patch test was removed by the researchers after 24 hours of contact with the skin, which was irradiated, and the reactions were annotated.

Result: the tests carried out evidenced the absence of skin sensitizations and no irritation process or sensitization process was identified during the study.

4. Dermatological Evaluation of the Topical Compatibility

This study has the function of proving the absence of the potential of primary dermal irritation, accumulated dermal irritation and the potential of dermal sensitization of the formulation.

For carrying out theses tests for allergenicity, 50 male and female volunteers with age ranging from 18 to 60 years were selected, excluding subjects who had any disease of the skin, injuries or nevus on the back and pregnancy or breast-feeding.

In order to carry out this study, the following material was used: semi-occlusive dressings composed by filter paper discs of 1.0 $cm^2$ duly identified, hypoallergenic semi-permeable sticking plaster for occlusion, physiological solution and samples of the cosmetic composition.

The following clinical researches were carried out:

I. Research on Primary Irritability 0.2 ml of the cosmetic composition was applied to each area of 1 $cm^2$ of the filter paper disc, and the saline solution was applied to the control disc. These discs were fixed to the volar face of the forearm of the volunteers with the aid of sticking plaster.

The test method used was the occlusive patch test. The test application places were the back of the volunteers, duly protected. The occlusive patch test was removed by the researches after 48 hours of contact with the skin, and the reactions were annotated 30 minutes after removal thereof.

II. Research on Accumulated Irritability

The sample was applied always in the same region, on the back, duly protected. Every 48 hours the volunteers returned for removal of the dressings, reading of the sites and re-application of the dressings in the same sites, for 3 consecutive weeks, in a total of 9 applications. The sample was re-applied onto the skin always at the same place, and the reactions were annotated.

III. Research on Sensitization

After the 9 consecutive applications, a two-week rest period followed, when no patch was applied. After this rest period, semi-occlusive dressings containing the product under study and the control were applied, in a virgin area, that is to say, a place where no patch had been applied. The test was removed by the researchers after 48 hours of contact with the skin, and the reactions were annotated 30 minutes after removal thereof.

After another 24 hours, the last reading was effected.

Result: no potential of primary dermal irritation, accumulated dermal irritation or dermal sensitization were observed.

5. Study of Stability—Oily-Alcoholic Galenic Form

The study of stability of cosmetic products has the objective of supplying data that indicate the degree of relative stability of a product under the ambient conditions to which they may be subjected from its manufacture to the end of its validity term.

In the study of stability of a product under conditions of accelerated aging, it is expected that, under some conditions, some variations in the evaluated parameters will occur; however, these variations should remain within the specified limits.

In the evaluation of stability of the finished product under conditions of accelerated aging, the following parameters were analyzed.

Physicochemical Parameters

Viscosity: the samples subjected to the conditions of 37° C., 5° C., 25° C., sunlight and 45° C. for 1 month kept the viscosity within the specified range (300-3000 cP);

Organoleptic Parameters

Appearance: the samples subjected to the conditions of 37° C., 5° C., 25° C., sunlight and 45° C. for 1 month did not present significant variations.

Color: the samples subjected to the conditions of 37° C., 5° C., 25° C., sunlight and 45° C. for 1 month did not present significant variations.

Odor: the samples subjected to the conditions of 37° C., 5° C., 25° C., sunlight and 45° C. for 1 month did not present significant variations.

III. The Compositions Used in the Test Described Hereinafter are Those Defined in Examples 3 and 4.

1. Study of Stability

In order to demonstrate the stability of the compositions of examples 3 and 4 (Gel sunscreen and Lip Protector), these samples were subjected for 3 months to the conditions: dark, ambient, light, 45° C., 37° C., 5° and −18° C.

In addition to viscosity analysis for the Gel Sunscreen, the study of stability included periodic evaluations of color, odor, appearance and microscopic analysis for both products.

The microscopic analysis used Optical Microscope Olympus, model BH-2 with condenser and light polarizer and the evaluations of viscosity the Brookfield Viscosimeter, model DV-II+.

Results: no significant alterations of color, odor and viscosity, separation of phases, exudation or crystallization, either visible to the naked eye or after microscopic evaluation of the samples subjected to the above-mentioned conditions were observed.

The invention claimed is:

1. A cosmetic non-emulsion composition, comprising a base selected from an oily-alcoholic medium and an oily-waxy medium, characterized by further comprising:
   triglyceryl-4 isostearate or an isomer thereof;
   dimethicone copolyol or a derivative thereof;
   at least one lipophilic substance having low or middle polarity that, at temperatures lower than 75° C., is in a liquid form; and
   at least one highly polar substance that forms intermolecular interactions by means of hydrogen bridges.

2. A cosmetic composition according to claim 1, characterized by comprising at least one electrolyte.

3. A cosmetic composition according to claim 1, characterized in that the triglyceryl-4 isostearate is present in an amount ranging from 0.001% to 10.000% by weight, based on the total weight of the cosmetic composition of the present invention.

4. A cosmetic composition according to claim 3, characterized in that the triglyceryl-4 isostearate is present in an amount ranging from 0.05% to 0.50% by weight, based on the total weight of the cosmetic composition of the present invention.

5. A cosmetic composition according to claim 1, characterized in that dimethicone copolyol is present in an amount ranging from 0.001% to 10.000% by weight, based on the total weight of the cosmetic composition of the present invention.

6. A cosmetic composition according to claim 5, characterized in that dimethicone copolyol is present in an amount ranging from 0.05% to 0.50% by weight, based on the total weight of the cosmetic composition of the present invention.

7. A cosmetic composition according to claim 1, characterized in that the lipophilic substance having low or middle polarity is present in an amount ranging from 0.01% to 99.8% by weight, based on the total weight of the cosmetic composition of the present invention.

8. A cosmetic composition according to claim 7, characterized in that the lipophilic substance having low or middle polarity is present in an amount ranging from 1.0% to 50.0% by weight, based on the total weight of the cosmetic composition of the present invention.

9. A cosmetic composition according to claim 1, characterized in that the highly polar substance is present in an amount ranging from 0.001% to 80.000% by weight, based on the total weight of the cosmetic composition of the present invention.

10. A cosmetic composition according to claim 9, characterized in that the highly polar substance is present in an amount ranging from 0.05% to 8.00% by weight, based on the total weight of the cosmetic composition of the present invention.

11. A cosmetic composition according to claim 2, characterized in that the electrolyte is present in an amount ranging from 0.001% to 5.000% by weight, based on the total weight of the cosmetic composition of the present invention.

12. A cosmetic composition according to claim 11, characterized in that the electrolyte is present in an amount ranging from 0.02% to 0.40% by weight, based on the total weight of the cosmetic composition of the present invention.

13. A pharmaceutical non-emulsion composition that comprises a base selected from an oily-alcoholic medium and an oily-waxy medium, characterized by further comprising:
   triglyceryl-4 isostearate or an isomer thereof;
   dimethicone copolyol or a derivative thereof;
   at least one lipophilic substance having low or middle polarity that, at temperatures lower than 75° C., is in a liquid form; and
   at least one highly polar substance that forms intermolecular interactions by means of hydrogen bridges.

14. A pharmaceutical composition according to claim 13, characterized by comprising at least one electrolyte.

15. A pharmaceutical composition according to claim 13, characterized in that the triglyceryl-4 isostearate is present in an amount ranging from 0.001% to 10.000% by weight, based on the total weight of the pharmaceutical composition of the present invention.

16. A pharmaceutical composition according to claim 15, characterized in that the triglyceryl-4 isostearate is present in an amount ranging from 0.05% to 0.50% by weight, based on the total weight of the pharmaceutical composition of the present invention.

17. A pharmaceutical composition according to claim 13, characterized in that dimethicone copolyol is present in an amount ranging from 0.001% to 10.000% by weight, based on the total weight of the pharmaceutical composition of the present invention.

18. A pharmaceutical composition according to claim 17, characterized in that dimethicone copolyol is present in an amount ranging from 0.05% to 0.50% by weight, based on the total weight of the pharmaceutical composition of the present invention.

19. A pharmaceutical composition according to claim 13, characterized in that the lipophilic substance having low or middle polarity is present in an amount ranging from 0.01% to 99.8% by weight, based on the total weight of the pharmaceutical composition of the present invention.

20. A pharmaceutical composition according to claim 19, characterized in that the lipophilic substance having low or middle polarity is present in an amount ranging from 1.0% to 50.0% by weight, based on the total weight of the pharmaceutical composition of the present invention.

21. A pharmaceutical composition according to claim 13, characterized in that the highly polar substance is present in an amount ranging from 0.001% to 80.00% by weight, based on the total weight of the pharmaceutical composition of the present invention.

22. A pharmaceutical composition according to claim 21, characterized in that the highly polar substance is present in an amount ranging from 0.05% to 8.00% by weight, based on the total weight of the pharmaceutical composition of the present invention.

23. A pharmaceutical composition according to claim 14, characterized in that the electrolyte is present in an amount ranging from 0.001% to 5.000% by weight, based on the total weight of the pharmaceutical composition of the present invention.

24. A pharmaceutical composition according to claim 23, characterized in that the electrolyte is present in an amount ranging from 0.02% to 0.40% by weight, based on the total weight of the pharmaceutical composition of the present invention.

25. A cosmetic product characterized by comprising a composition as defined in claim 1.

26. A pharmaceutical product characterized by comprising a pharmaceutical composition as defined in claim 13.

27. A process for preparing a cosmetic composition or a pharmaceutical composition, characterized by comprising the following steps:
- a) in a first container, incorporating a lipophilic substance having low or middle polarity, triglyceryl-4 isostearate or an isomer thereof and dimethicone copoliol or a derivative thereof, under stirring of 500 to 2,000 rpm;
- b) keeping the stirring for 5 to 30 minutes until complete limpidity of this phase is achieved;
- c) adding a highly polar substance, totally solubilized; and
- d) keeping the stirring for about 15 minutes.

28. A process according to claim 27, characterized in that all the steps are conducted at a temperature ranging from 20 to 30° C.

29. A process according to claim 27, characterized in that, after the step d), other components are added to the mixture in order to prepare the cosmetic or pharmaceutical composition desired.

30. A process according to claim 29, characterized by comprising the additional step of:
- incorporating the mixture obtained at the end of the preparation of the cosmetic or pharmaceutical composition under naval stirring of 500 to 2,000rpm.

31. A cosmetic composition characterized by being obtainable by the process as defined in claim 27.

32. A pharmaceutical composition characterized by being obtainable by the process as defined in claim 27.

* * * * *